United States Patent [19]
Cooper

[11] Patent Number: 5,207,639
[45] Date of Patent: May 4, 1993

[54] FETAL LUNG APPARATUS

[76] Inventor: William I. Cooper, 300 N. Fourteenth St., Easton, Pa. 18042

[21] Appl. No.: 658,697

[22] Filed: Feb. 21, 1991

[51] Int. Cl.⁵ .................. A61M 37/00; A61G 10/00; A61G 10/02; A61G 11/00
[52] U.S. Cl. ............................................ 604/4; 604/5; 600/21; 600/22
[58] Field of Search ................. 604/4, 415, 53; 128/DIG. 3; 600/21, 22

[56] References Cited

U.S. PATENT DOCUMENTS

| | | | |
|---|---|---|---|
| 2,809,065 | 5/1974 | Gatts | 600/22 |
| 2,842,124 | 7/1958 | James | 604/4 X |
| 3,335,713 | 8/1967 | Grosholz et al. | 600/22 |
| 3,482,575 | 12/1969 | Claff et al. | 604/4 |
| 3,682,172 | 8/1972 | Freedman et al. | 604/5 |
| 3,893,444 | 7/1975 | Fatt | 128/635 |
| 3,934,982 | 1/1976 | Arp | 128/DIG. 3 |
| 3,993,042 | 11/1976 | Gatts | 600/22 |
| 4,079,728 | 3/1978 | Gatts | 600/22 |
| 4,088,124 | 5/1978 | Korner et al. | 600/22 |
| 4,186,457 | 2/1980 | Amelung | 600/22 X |
| 4,281,425 | 8/1981 | Jacobs | 600/22 X |
| 4,457,747 | 7/1984 | Tu | 604/4 |
| 4,583,969 | 4/1986 | Mortensen | 604/4 X |
| 4,828,543 | 5/1989 | Weiss et al. | 604/4 |
| 4,838,855 | 6/1989 | Lynn | 604/4 X |
| 4,850,954 | 7/1989 | Charvin | 604/4 |
| 4,865,583 | 9/1989 | Tu | 604/53 |
| 5,006,105 | 4/1991 | Sherard | 600/22 |
| 5,100,375 | 3/1992 | Koch | 600/22 |

Primary Examiner—David Isabella
Assistant Examiner—Elizabeth M. Burke
Attorney, Agent, or Firm—Pollock, Vande Sande and Priddy

[57] ABSTRACT

Apparatus for oxygenating the blood of a non-breathing prematurely born baby which is still attached to its umbilical cord. The apparatus includes a lung member for oxygenating blood, and an adapter for connecting venous and arterial blood vessels in the umbilical cord with the blood inlet and outlet of the lung machine.

3 Claims, 1 Drawing Sheet

FETAL LUNG APPARATUS

The present invention relates to apparatus for supporting the life of a prematurely-born baby.

BACKGROUND OF THE INVENTION

Babies which are born after about a 10-week gestation period typically are capable of functioning independently of the mother from a hormonal standpoint, and at this stage, the only maternal functions are to supply oxygen and nutrients to the fetus, and to remove waste byproducts, such as uric acid. However, until a gestation period of about 28 weeks, lungs are not sufficiently developed to support the baby; consequently, babies born before the 28th week, as by irreversible premature labor, have had little chance to survive.

SUMMARY OF THE INVENTION

It is accordingly one object of this invention to provide apparatus for supporting the life of a baby which is born too prematurely to have functioning lungs.

It is another object of the invention to provide apparatus for oxygenating the blood of a non-breathing premature baby.

Other objects of this invention will be apparent from the following description and the claims appended hereto.

In accordance with the present invention, there is provided apparatus for oxygenating the blood of a non-breathing premature baby, the blood passing between the apparatus and the baby through the baby's umbilical cord. The apparatus includes a lung machine and an adapter for interconnecting blood vessels in the umbilical cord with an oxygen-depleted blood inlet and an oxygenated blood outlet of the lung machine. Means are provided for suspending the baby the manner in which the baby had been living before its premature birth.

This invention takes advantage of the changes in maternal functions with respect to the fetus as it develops, and also takes advantage of the pumping action of the baby's heart to circulate the blood from the baby, through the apparatus, and back to the baby. Fetal blood is thus continuously circulated by the fetal heartbeat. The fetus also urinates and is developing a normal kidney function, thus providing its own method of cleaning its blood of toxins.

This device provides an extra-uterine environment for a baby whose mother had been Rh sensitized, in which case, her antibodies would endanger the baby by destroying its red blood cells.

DETAILED DESCRIPTION OF THE INVENTION

Figure 1:
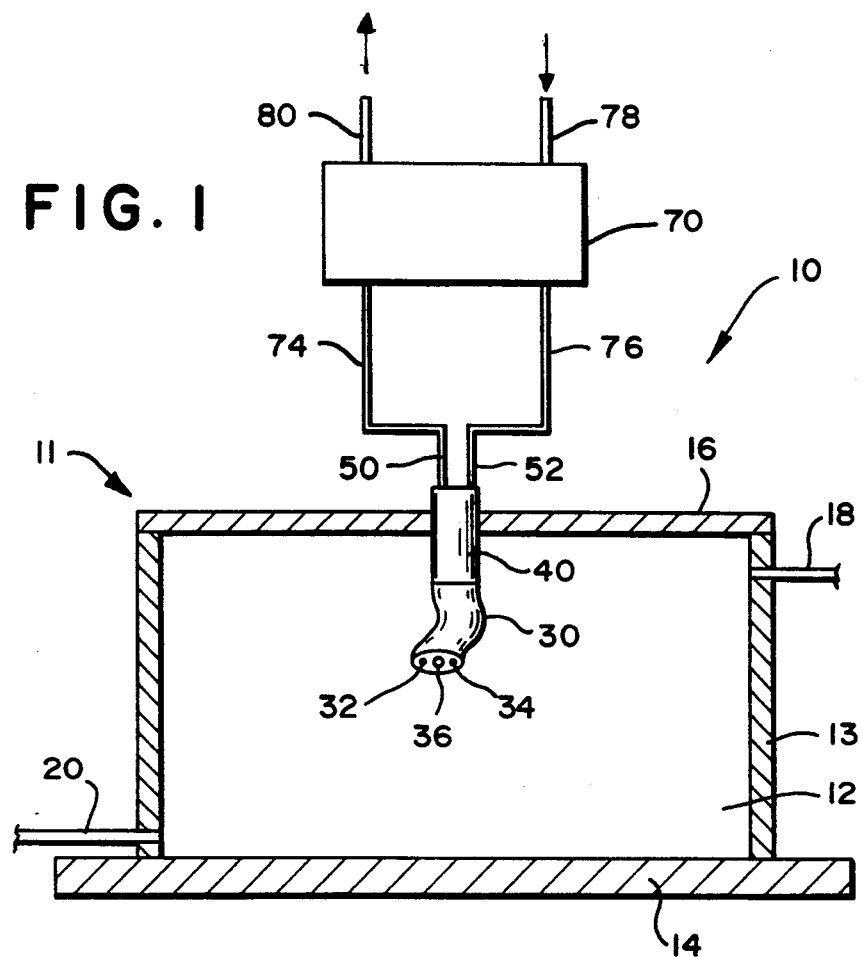
FIG. 1 is a vertical sectional view of one embodiment of the present invention.

The present invention replaces the function of the uterus after the baby, umbilical cord and placenta have been surgically removed by hysterectomy in a sterile environment. The placenta is then separated from the umbilical cord and the baby, with its attached umbilical cord, is secured within the life support system of the present invention.

In the embodiment of the present invention shown in the Figures, life support system 10 includes chamber 11 for containing a physiological fluid 12 in which the premature baby is to be suspended, a lung machine 70 for oxygenating the baby's blood, and an adapter 40 for interconnecting the blood vessels 32, 34, 36 in umbilical cord 30 with blood conduits 74, 76 from lung machine 70.

Chamber 11 for containing a physiological fluid 12 includes base 14, side wall 13 and top 16. Means, not shown, are provided in top 16 for access to the interior of chamber 11. Fluid inlet 18 is provided for introducing physiological fluids into chamber 11 and fluid outlet 20 is provided for removing fluid. The flow rate is not critical and a flow rate of about one liter per hour is suitable. The physiological fluid 12 is sterile, salt balanced, and mimics the amniotic fluid in which the baby had been living. Such fluids are available on the market and one which may be used is lactated ringers solution with or without additions.

Figure 3:
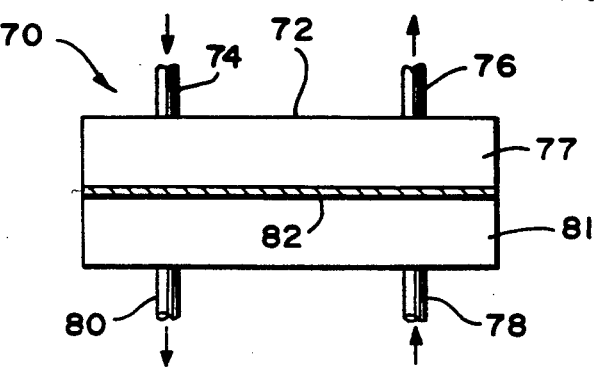
FIG. 3 is a representation of a lung machine for use in the present invention.

Lung machines which may be used in the present invention are well-known in the art, and FIG. 3 is provided to illustrate the salient features of such a machine. A lung machine 70 includes a housing 72 having blood chamber 77 separated from oxygen chamber 81 by membrane 82. Blood chamber 77 is provided with inlet port 74 for oxygen-depleted blood and outlet port 76 for oxygenated blood. Chamber 81 is provided with oxygenating gas inlet port 78 and oxygen and carbon dioxide outlet port 80.

The membrane 82 is depicted as a flat sheet. However, it may be in the form of a plurality of small diameter tubes or a plurality of flat sheets. The properties desired in a blood oxygenator membrane include good gas permeability with respect to gaseous oxygen and carbon dioxide, chemical stability, blood compatibility or substantially nonthrombogenic behavior in blood-containing environments, sufficiently hydrophobic to serve as a water vapor barrier, non-toxic, relative inertness to body fluids, and sufficient mechanical properties for use in blood oxygenating devices. U.S. Pat. No. 3,969,240 to Kolobow et al describes the use of polysiloxanes as membranes for use in an artificial lung; U.S. Pat. No. 4,008,047 to Petersen describes the use of ethylcellulose, and in particular fluorinated ethylcellulose as membranes for artificial lungs; and, U.S. Pat. No. 4,093,515 to Kolobow describes the use of a carbon-containing silicone rubber as a membrane for use in an artificial lung. The disclosures in these patents of materials useful in a lung machine are hereby incorporated by reference.

The membranes may be in the form of a relatively flat sheets or a plurality of sheets, or may be in the form of small diameter tubes such as, for example, capillary tubes, as described in U.S. Pat. Nos. 4,231,878 to Esmond, 4,239,729 to Hasagawa et al, 4,639,353 to Takamura et al, and 4,781,889 to Fukusawa et al. The disclosures in these patents of membrane structures are hereby incorporated by reference.

Lung machine 70 may have associated with it means (not shown) for controlling the temperature of the blood flowing through the circuit. U.S. Pat. No. 4,791,054 to Hamada et al relates to a blood oxygenating device including a heat exchanger, in which the membranes are in the form of tubes. The disclosure of Hamada et al of a typically useful lung machine is hereby incorporated by reference.

Figure 2:
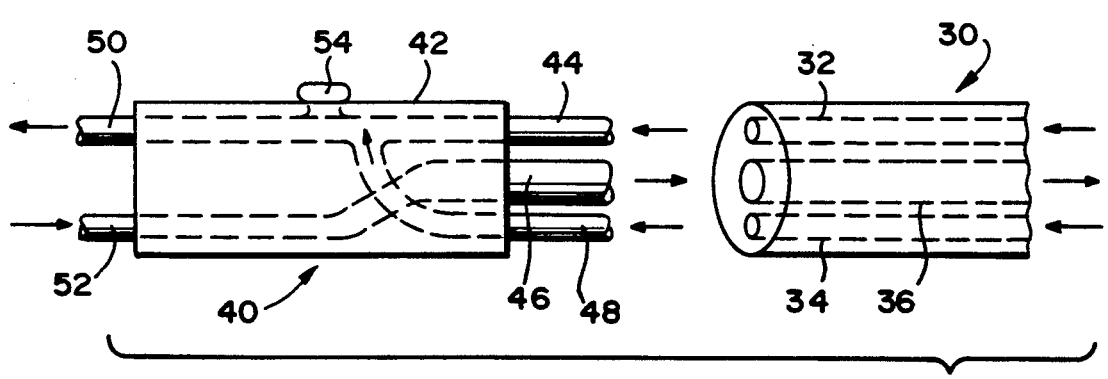
FIG. 2 is a sectional view of a device for interconnecting the umbilical cord and the lung machine, showing its arrangement with the umbilical cord.

Adapter 40 and its relationship to the umbilical cord is shown in more detail in FIG. 2. As shown therein, arterial stubs 44, 48 are adapted for insertion into arterial vessels 32 and 34, respectively, of umbilical cord 30. Venous stub 46 is adapted for insertion into venous vessel 36 of the umbilical cord 30. In the preferred form of the invention, these stubs 44, 46, 48 are long enough and flexible enough to go into the umbilical cord vessels at least several inches, and preferably will have a flanged end (not shown) so that when fitted properly, they will be snug within the vessels, thus preventing leakage of blood. The umbilical cord 30 will be sutured to the adapter 40 to secure it in place and to help prevent blood loss. Once the cut portion of the umbilical cord is healed sufficiently, there will be no blood loss or seepage at the site of the adapter.

As shown in FIG. 2, tubes 44 and 48 of adapter 40 carry incoming blood from the umbilical arteries, and merge in adapter 40 to a single tube 50. The tube 50 is parallel to the tube 46 carrying blood to umbilical cord vein 36.

As shown in FIG. 2, adapter 40 is provided with a rubber-capped port 54, which, although shown in tube 50, could be in either the venous or arterial blood tubes. Nutrients which may be introduced through capped port 54 are substantially the same in composition as the liquids given in feeding intravenously by hyperalimentation. The rate of feeding nutrients may range from 1 to 10 ml/hour, depending on the size of the baby. Port 54 could be used for monitoring oxygenation levels and concentrations of various blood components, transfusing blood and adding medication to the blood.

What is claimed is:

1. Apparatus for oxygenating oxygen-deficient blood of a non-breathing premature baby still attached to an umbilical cord and separated from a placenta, the umbilical cord having arterial blood vessels and a venous blood vessel, said apparatus comprising, in combination:

a) a lung machine comprising a housing forming an oxygenator chamber, said chamber having oxygen-deficient blood inlet means, means for oxygenating said blood, and oxygenated blood outlet means;

b) adapter means configured for fitting the umbilical cord comprising an elongated housing having first and second end portions and first and second passage means extending between said first and second end portions, said first passage means configured to be in fluid communication at said first end portion with said blood outlet means of said lung machine and at said second end portion with the venous blood vessel, and said second passage means configured to be in fluid communication at said first end portion with said blood inlet means of said lung machine and at said second end portion with the arterial blood vessels; and, c) a tank operatively connected to said adapter means for suspending the baby and the umbilical cord in a physiological fluid while said blood is being oxygenated in said lung machine, said tank having fluid inlet means for introducing physiological fluid therein, and fluid outlet means for removing physiological fluid from said tank.

2. Apparatus according to claim 1 wherein said lung machine includes means for controlling blood temperature.

3. Apparatus according to claim 1 wherein said adapter means includes means for introducing body treating fluids into said blood.

* * * * *